(12) United States Patent
Hauger

(10) Patent No.: US 9,913,752 B2
(45) Date of Patent: Mar. 13, 2018

(54) SURGICAL DEVICE AND SURGICAL METHOD

(75) Inventor: Christoph Hauger, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 962 days.

(21) Appl. No.: 13/470,680

(22) Filed: May 14, 2012

(65) Prior Publication Data

US 2012/0226267 A1 Sep. 6, 2012

Related U.S. Application Data

(63) Continuation of application No. PCT/EP2010/006935, filed on Nov. 15, 2010.

(60) Provisional application No. 61/261,249, filed on Nov. 13, 2009.

(30) Foreign Application Priority Data

Nov. 13, 2009 (EP) .................................... 09014235

(51) Int. Cl.
   *A61B 18/20* (2006.01)
   *A61F 9/007* (2006.01)
   *A61B 3/10* (2006.01)

(52) U.S. Cl.
   CPC .......... *A61F 9/00745* (2013.01); *A61B 3/102* (2013.01); *A61B 3/1005* (2013.01)

(58) Field of Classification Search
   CPC ........ A61B 19/52; A61B 2017/320072; A61B 17/320068; A61B 18/1477; A61B 3/1005; A61B 3/102; A61F 9/00745
   See application file for complete search history.

(56) References Cited

U.S. PATENT DOCUMENTS

| 5,651,783 A | 7/1997 | Reynard |
| 6,134,003 A | 10/2000 | Tearney et al. |
| 6,501,551 B1 | 12/2002 | Tearney et al. |
| 6,533,750 B2 | 3/2003 | Sutton et al. |
| 6,564,087 B1 | 5/2003 | Pitris et al. |
| 8,401,610 B2 * | 3/2013 | Milner et al. ................ 600/407 |

(Continued)

OTHER PUBLICATIONS

Dan Z. Reinstein et al., "Correlation of Anterior Chamber Angle and Ciliary Sulcus Diameters With White-to-White Corneal Diameter in High Myopes Using Artemis VHF Digital Ultrasound", Journal of Refractive Surgery, vol. 25, No. 2, Feb. 2009, pp. 1-10.

(Continued)

*Primary Examiner* — Scott T Luan
(74) *Attorney, Agent, or Firm* — Patent Portfolio Builders PLLC

(57) ABSTRACT

A surgical instrument system for ophthalmic surgery in an eye is provided, comprising: an OCT apparatus including an interferometer; an optical fiber coupled to the OCT apparatus and extending a probe arm of the interferometer; a hand tool comprising: a hand piece, a tube extending away from the hand piece and comprising a distal end portion having a longitudinal axis, wherein a distal portion of the optical fiber is received within the tube; a beam emitter coupled to a tip end of the optical fiber and configured to emit an OCT measuring beam into an emission direction; and an actuator configured to change the emission direction of the OCT measuring beam relative to a tip end of the distal end portion.

33 Claims, 7 Drawing Sheets

(56) References Cited

U.S. PATENT DOCUMENTS

| | | | |
|---|---|---|---|
| 2003/0004412 A1 | 1/2003 | Izatt et al. | |
| 2005/0251116 A1* | 11/2005 | Steinke et al. | 606/8 |
| 2006/0106370 A1* | 5/2006 | Baerveldt et al. | 606/4 |
| 2008/0269642 A1 | 10/2008 | Deacon et al. | |
| 2009/0157062 A1 | 6/2009 | Hauger et al. | |

OTHER PUBLICATIONS

Extended European Search Report issued in corresponding European application No. 09 014 235.7 dated Feb. 24, 2010.

International Search Report issued in corresponding International application No. PCT/EP2010/006935 dated Mar. 21, 2011.

Written Opinion issued in corresponding International application No. PCT/EP2010/006935 dated Mar. 21, 2011.

T. Kohnen et al., "Aktueller Stand der Refraktiven Chirurgie—Möglichkeiten und Ergebnisse", Orthoptik—Pleoptik 30/2006/2007; Nov. 19, 2005; pp. 1-12.

T. H. Neuhann, "Implantate und Verfahren in der Augenheilkunde", Medizintechnik—Life Science Engineering, Springer, 2009, pp. 1987-2013.

J. Kuchenbecker et al., "Phake Intraokularlinsen (PIOL)—eine aktuelle Übersicht"; [downloaded from http://www.med.uni-magdeburg.de/fme/kauge/PIOL.pdf on Mar. 25, 2013]; pp. 9-10, 12-14.

alz Augenklinik München, "Phake Linsen"; [downloaded from http://www.gutsehen.de/refraktivechirurgie/alz_phake_linsen.pdf on Mar. 24, 2013]; pp. 1-12.

G. U. Auffarth, "Phake Intraokularlinsen", Ophthalmologe, vol. 101, No. 3, Springer, 2004, pp. 229-231; Heidelberg, Germany.

T. Kohnen et al., "Basiswissen refraktive Chirurgie", Deutsches Ärzteblatt, vol. 105, No. 9, Feb., 2008, pp. 163-172.

G. U. Auffarth, "Akkommodative Intraokularlinsen", Ophthalmologe, vol. 99, No. 11, Springer, Nov. 2002, pp. 809-810.

* cited by examiner

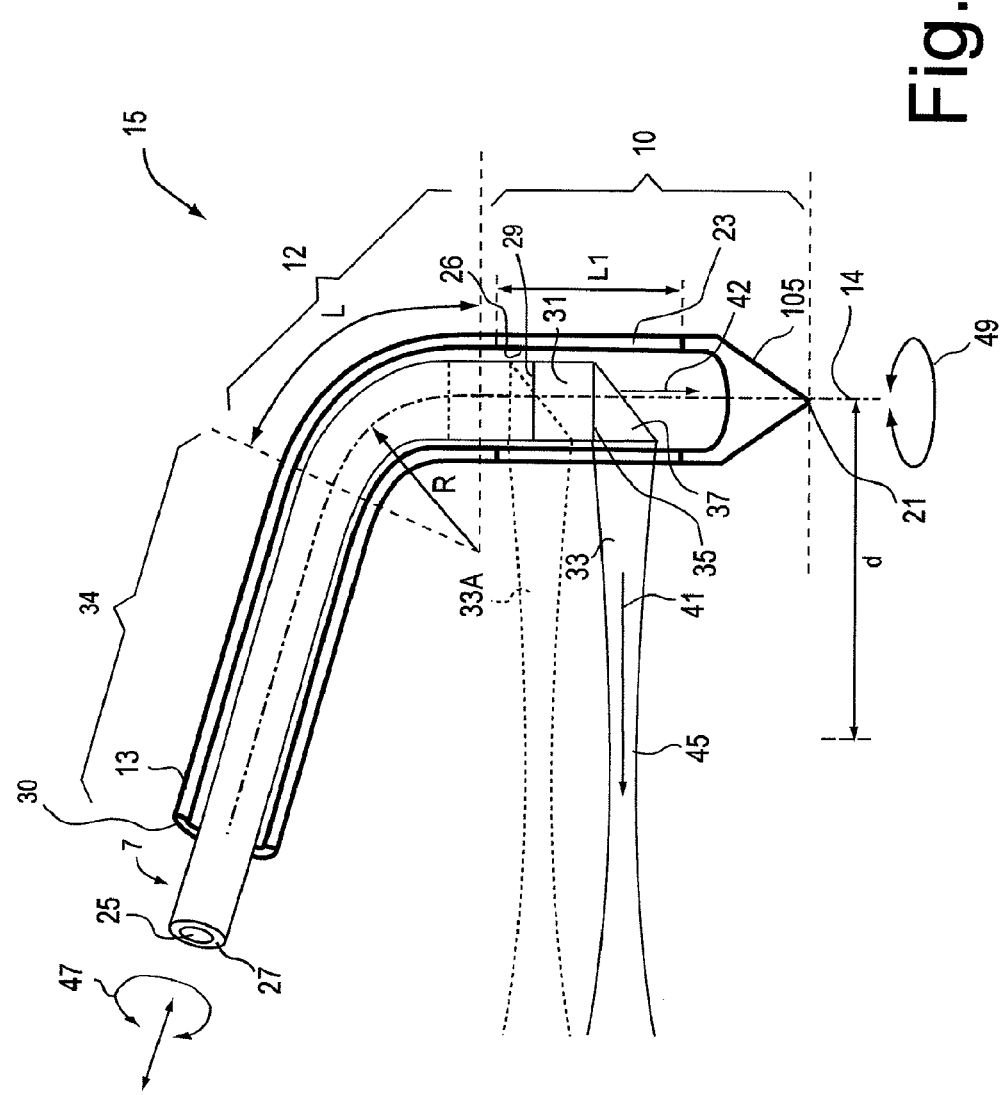

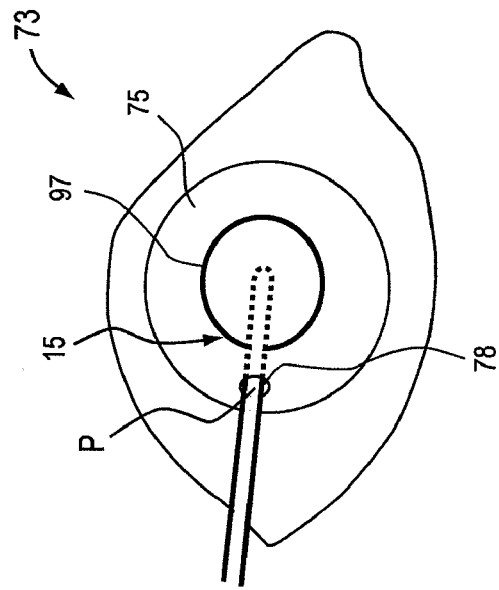
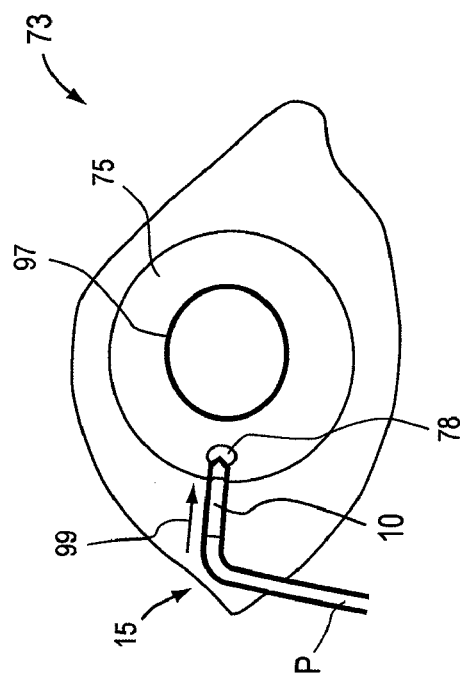

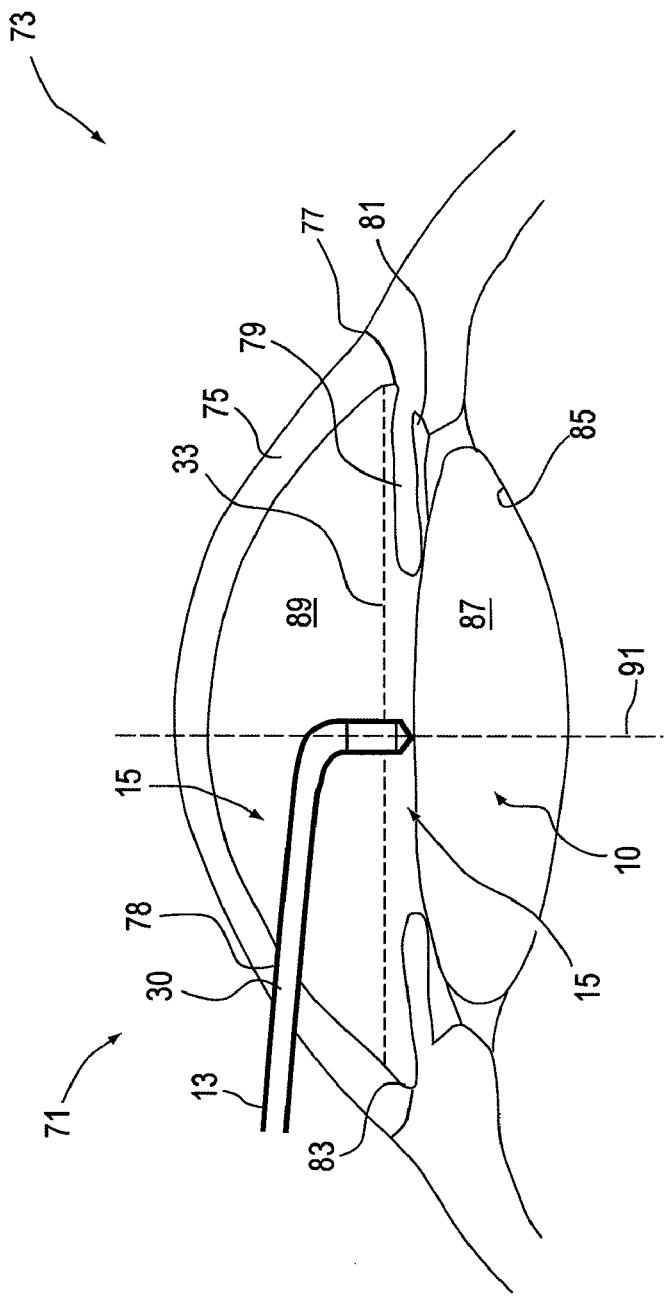

SURGICAL DEVICE AND SURGICAL METHOD

CROSS-REFERENCES TO RELATED APPLICATIONS

The present application is a bypass-continuation of international patent application PCT/EP2010/006935, which claims priority of Patent Application No. EP 09 014 235 filed on Nov. 13, 2009 with the European Patent Office and entitled "Surgical Device and Surgical Method" and of Provisional Patent Application No. 61/261,249, filed on Nov. 13, 2009 in the United States of America, the contents of both documents is hereby incorporated by reference in their entirety.

FIELD

The invention relates to surgical devices and surgical methods in general. In particular, the invention relates to a surgical instrument system and a surgical method for performing cataract surgery.

BACKGROUND

In a cataract surgery, a phacoemulsification needle is inserted into the capsular bag of a patient's eye through the cornea and the anterior chamber. Ultrasonic energy is supplied to the needle to emulsify the crystal lens of the eye. Emulsified pieces of the crystal lens are aspirated by the needle, and viscoelastic fluid is supplied through the needle into the capsular bag. An intraocular lens (IOL) is inserted into the capsular bag after the crystal lens has been removed by such processing.

In other techniques of eye surgery, a phakic intraocular lens (PIOL) is inserted into the anterior chamber of the eye or into the posterior chamber of the eye, without removing the crystal lens of the eye.

To obtain an optimal result in such surgery, where an intraocular lens is implanted into the anterior chamber, the posterior chamber or the capsular bag, it is important to select an intraocular lens of a size suitable for a patients eye. Lens sizes for anterior chamber phakic intraocular lenses and for posterior chamber phakic intraocular lenses have commonly been estimated by adding 0.5 to 1.0 mm to the horizontal white-to-white corneal diameter. However, the white-to-white corneal diameter is not a reliable indicator for the angle diameter of the anterior chamber and the sulcus diameter, also referred to as sulcus-to-sulcus diameter, of the posterior chamber. In particular, it is difficult to determine the sulcus diameter and the diameter of the capsular bag from outside of the eye since the iris prevents optical measurements of the corresponding tissue portions of the eye.

It is desirable to provide methods and systems suitable for measuring geometries of eye tissues.

SUMMARY

According to embodiments, a surgical instrument system for ophthalmic surgery in the interior of an eye is provided, comprising: an OCT apparatus including an interferometer; an optical fiber coupled to the OCT apparatus and extending a probe arm of the interferometer, the optical fiber having a tip end; a hand tool comprising: a hand piece, a tube extending away from the hand piece and comprising a distal end portion having a longitudinal axis and a tip end, wherein a distal portion of the optical fiber is received within the tube; a beam emitter coupled to the tip end of the optical fiber and configured to emit an OCT measuring beam into an emission direction of the emitter; and an actuator configured to change the emission direction of the OCT measuring beam relative to the tip end of the distal end portion.

The hand piece may be designed to be graspable with one or two hands of a user. The hand tool may further be designed such that the distal end portion is insertable into the eye through an opening in the cornea. The beam emitter may be located within the distal end portion of the tube.

The surgeon can manipulate the hand tool by grasping the hand piece with one or two hands to insert the tube into the eye such that the distal end of the tube is positioned at a location suitable for performing the OCT measurement of the eye tissues. The OCT measurement is performed by directing the OCT measuring beam into different directions from the emitter.

According to exemplary embodiments, the hand tool also provides the function of a phacoemulsificator. For this purpose, the hand tool may comprise an ultrasonic transducer to vibrate a tip end of the tube and/or a needle extending adjacent to the tube.

The distal end portion of the tube comprises a longitudinal axis. The longitudinal axis may be defined as a central axis such that opposing side walls of the tube end portion have a same or substantially the same radial distance from the longitudinal axis. A portion of the longitudinal axis may be curved. An outer diameter of the distal end portion of the tube may be for example be between 0.8 mm and 2 mm or between 0.8 mm and 1.5 mm or between 0.8 mm and 1.2 mm. A diameter of a core of the optical fiber may be for example between 8 and 10 micrometers.

The optical fiber may comprise a core and a cladding. The core of the optical fiber may be surrounded by the fiber cladding. The core of the optical fiber and the fiber cladding may be received within the tube. An outer diameter of the fiber cladding may be within 200 and 400 micrometers, or between 200 and 300 micrometers.

The beam emitter may be located on the longitudinal axis. The beam emitter may be located within the distal end portion. The beam emitter may be configured such that the emission direction of the emitter is oriented transverse, in particular perpendicular to a tangent to the longitudinal axis of the distal end portion at the position of the beam emitter. The distal end portion may be configured such that the OCT measuring beam of the OCT apparatus is emitted from the beam emitter and transmitted through side walls of the distal end portion.

Accordingly, there is provided a surgical instrument system, which allows to insert the distal end portion of the tube into an eye under examination. Thereby, it is possible to image interior portions of the eye by OCT. It is further possible to acquire OCT image data without moving the tube. Thereby, OCT scans are conductable at a fixed and defined position of the tube. A position of the distal end portion of the tube within the eye may be adjusted under observation by a microscope. Then, an OCT scan may be acquired at the adjusted position.

According to an embodiment, the distal end portion comprises an axial end section having a transparent tubular section, which is transparent for measuring light of the OCT measuring beam, wherein a length of the transparent tubular section is within a range of 1 mm to 6 mm, or within a range of 3 mm to 6 mm, or within a range of 3.5 mm to 5 mm, or within a range of 1 mm to 3 mm, or within a range of 1 mm to 2 mm.

With the transparent tubular section being within the range of 3 mm to 6 mm or within the range of 3.5 mm to 5 mm, it is possible to measure the entire geometry of the capsular bag. A shorter length of the transparent tubular section in the range of 1 mm to 3 mm, or within a range of 1 mm to 2 mm allows to image for example a specific portion of the capsular bag, the structure of the anterior chamber angle or the structure of the ciliary sulcus. A small length of the transparent tubular section has the advantage that the distal end portion is more easily insertable into and maneuverable within the interior of the eye.

The beam emitter may be located within the transparent tubular section. The transparent tubular section may be defined as a tubular section which is transparent along its full length and which is further transparent along its full perimeter. A longitudinal axis of the transparent tubular section may correspond to a portion of the longitudinal axis of the distal end portion within the transparent tubular section. The transparent tubular section may be configured such that OCT measuring light of the OCT measuring beam is transmittable from inside the tube to outside the tube from each position on the longitudinal axis within the transparent tubular section and along the emission direction. A portion of the OCT measuring light may be reflected or absorbed in the transparent tubular section. A transparency of the transparent tubular section may be such that tissues of the interior of the eye are imageable with the OCT apparatus when the distal end portion is placed in the interior of the eye. For example, the transparent tubular section may be made at least partially from glass and/or transparent plastic material.

Accordingly, it is possible to perform 360-degree B-scans by using the OCT apparatus for accurately imaging extended tissue portions within the interior of the eye.

According to a further embodiment, a radius of curvature of the longitudinal axis at each point within the transparent tubular section is greater than 15 mm, in particular greater than 20 mm or greater than 30 mm.

Accordingly, since the radius of curvature of the longitudinal axis at each point within the transparent tubular section is comparatively large, it is possible to easily reconstruct the structure of the imaged tissue of the interior of the eye without having to perform time-consuming data correction routines for aligning individual planes of the B-scans relative to each other. In case the radius of curvature of the longitudinal axis at each point within the transparent tubular section is known, OCT data, obtained by performing the OCT scans may be corrected depending on the determined radius of curvature. Moreover, it is possible to align the longitudinal axis within the transparent tubular section with the main axis of the eye. Thereby, for example, it is possible to adjust the position of the longitudinal axis within the transparent axial section such that the transparent tubular section has substantially the same distance from each portion of the ciliary sulcus. Thereby, it is possible to measure the structure of the ciliary sulcus with high precision. The main axis of the eye may be an optical axis of the lens of the eye.

According to an embodiment, the beam emitter is located within the transparent tubular section and the actuator is configured to displace the emitter relative to the tube along the longitudinal axis and over the length of the transparent tubular section.

Accordingly, it is possible to perform B-scans in a plurality planes, which intersect the longitudinal axis at different positions. Thereby, for example, it is possible to measure the structure of tissues, which extend along the main axis of the eye. Examples of such tissues are the capsular bag, the ciliary sulcus and/or the angle of the anterior chamber.

According to a further embodiment, a first tangent to the longitudinal axis at a proximal end of the distal end portion and a second tangent to the longitudinal axis at a tip end of the distal end portion form a bending angle of the distal end portion of between 60 and 100 degrees, or between 70 and 100 degrees, or between 70 and 95 degrees, or between 80 and 95 degrees, or between 85 and 90 degrees.

Accordingly, it is possible to insert the distal end portion of the tube into the interior of the eye at a portion of the cornea, which is distant from the main axis of the eye. Through the range of the bending angle, the position of the portion of the cornea, through which the distal end portion of the tube is inserted, may be optimized. Also, it is possible for the user to adjust the position of the distal end portion within the eye under observation of a microscope. The optical axis of the microscope may be aligned substantially parallel to the main axis of the eye. Thereby, it is possible for the user to accurately align with the main axis of the eye, the portion of the longitudinal axis, which is within the transparent tubular section. Thereby, structures like the ciliary sulcus, the anterior chamber angle of the capsular bag are arranged within the measurement range of the OCT apparatus. Therefore, structures such as the ciliary sulcus, the anterior chamber angle and the capsular bag are measurable with high precision.

Furthermore, since it is possible to insert the distal end portion into the eye through an opening in the cornea, which is distant from the main axis of the eye, the portion of the cornea, which is close to the main axis, is not affected by the opening. Therefore, the vision is less likely to be affected by the opening. Also, since the opening in the cornea is distant from the main axis of the eye, the opening may be formed large enough such that also the intraocular lens is insertable through this opening. Therefore the surgical instrument system allows to image the interior of the eye by using the opening in the cornea, through which the intraocular lens is later inserted. Thereby, no additional opening is necessary.

According to a further embodiment, a first distance between an intersection point of the first tangent with the second tangent and the proximal end is between 4.5 mm and 8 mm, or between 5 mm and 7 mm, or between 5 and 6 mm. According to a further embodiment, a second distance between the intersection point and the tip end is between 3 and 9 mm, or between 5 and 9 mm, or between 5 mm and 8 mm, or between 5 mm and 7 mm, or between 3 mm and 6 mm.

A shorter range of the distance of the tip end from the intersection point may be suitable for a shorter transparent tubular section, which is optimized for imaging portions of tissues, which have a small extend along the main axis of the eye.

According to a further embodiment, the distal end portion consists of or comprises an axial end section, a curved axial section and a proximal axial section, wherein the curved axial section is located between the axial end section and the proximal axial section. The curved axial section may be in contact with the axial end section and the proximal axial section.

According to a further embodiment, for each point on the longitudinal axis within the curved axial section, a radius of curvature of the longitudinal axis is within a range of 1 mm to 6 mm. A radius of curvature of the longitudinal axis at each point within the axial end section and/or the proximal axial section may be greater than 15 mm, or greater than 20 mm, or greater than 30 mm.

According to a further embodiment, a length of the proximal axial section is in a range of between 3 mm and 6 mm. According to a further embodiment, a length of the curved axial section is in range of between 2 mm and 8 mm. According to a further embodiment, a length of the proximal axial section is in a range of between 3 mm and 6 mm. The lengths may be measured along the longitudinal axis. A proximal end of the proximal axial section may be the proximal end of the distal end portion.

According to a further embodiment, the hand piece is configured to rotate the distal end portion about a rotation axis, which is aligned with the first tangent.

The hand piece may be configured to rotate the distal end portion by at least 90 degrees about the rotation axis. The hand piece may comprise one or more rotation actuators which are arranged at the tube. The rotation actuators may be configured to be controllable, and the distal end portion is rotated upon operation of the rotation actuators. Furthermore, the surgical instrument system may comprise a controller which is in signal communication with the rotation actuators and which is configured to control the operation of the rotation actuators. Thereby for example, a user may rotate the tube by operating a button.

Accordingly, it is possible to easily and controllably rotate the distal end portion during the inserting of the tube end portion through the opening in the cornea into the interior of the eye. Thereby, it is possible to insert the distal tube end section into the interior of the eye without causing unintended damage to the interior tissues of the eye.

According to an embodiment, a bending stiffness of the distal end portion is such that the distal end portion is insertable into the interior of the eye through an opening in a cornea of the eye.

In particular, the bending stiffness may be such that the force, which is required for inserting the distal end portion through the opening in the cornea, may be applied through operating the hand piece.

According to a further embodiment, the tip end of the distal end portion is displaced by less than 1.5 mm or less than 1 mm, or less than 0.5 mm when a force of 0.25 N is applied to the tip end of the distal end portion and the proximal end is held stationary.

The force which is applied to the tip end may refer to forces, which are applied in a direction, which is oriented perpendicular to a tangent to the longitudinal axis at the tip end of the distal end portion. However, it is also conceivable, that the force refers to forces in any direction. When measuring the displacement, the proximal end of the distal end portion is held stationary, for example by a clamp.

Accordingly, a distal end portion is provided, which has a sufficiently high bending stiffness such that the distal end portion is insertable through the opening in the cornea of the eye. Moreover, the tip end does not or only insignificantly move when the optical fiber is rotated about the longitudinal axis or moved along the longitudinal axis when performing the OCT scans. For example, the distal end portion may be configured such that the emitter does not move more than 5 micrometer when being rotated during a scan. Therefore, a distal end portion having a high bending stiffness does not deteriorate the resolution of the OCT image. In particular, OCT scans of tissue structures, which have a distance of approximately 6.5 mm from the portion of the longitudinal axis which is located within the transparent tubular section, can be acquired with a high resolution.

The transparent tubular section may be made at least partially of glass and/or transparent plastic material. The portion of the distal end portion between the transparent tubular section and the proximal end may be made at least partially of metal.

According to an embodiment, the actuator is configured to rotate the optical fiber about the longitudinal axis of the distal end portion and/or to move the optical fiber along the longitudinal axis of the distal end portion.

The OCT measurement is performed by directing the OCT measuring beam into different directions from the emitter. The actuator may be configured to rotate the beam emitter at each of a plurality of different positions about the longitudinal axis of the distal end portion. An internal diameter of side walls of the axial end section and an external diameter of the fiber cladding which surrounds the optical fiber may be configured such that the optical fiber is guided by the side walls. Within the distal end portion, the longitudinal axis of the fiber may correspond to the longitudinal axis of the distal end portion. The OCT apparatus may be configured to perform, at each of the plurality of different axial positions of the beam emitter, an OCT scan by rotating the fiber about the longitudinal axis. For example, the actuator may be configured to rotate the optical fiber by 360 degrees about the longitudinal axis and the OCT apparatus may be configured to conduct a 360-degree B-scan during the rotation of the fiber. The plurality of B-scans, which correspond to the plurality of different axial positions represent an OCT scan of a volume of tissues of the eye. The scanned volume may comprise the ciliary sulcus, the anterior chamber angle and/or portions of the capsular bag.

According to exemplary embodiments, the emitter is rotated about the longitudinal axis by 360 degrees to obtain an OCT B-scan of one plane. The beam emitter is then translated in a direction of extension of the distal end portion of the tube, i.e. translated along the longitudinal axis, and a next B-scan is obtained in a next adjacent plane. This process is repeated to obtain a sufficiently high number of B-scans to generate an image of a sufficient volume of the eye tissues, allowing to determine the desired geometric values of the eye, such as the diameter of the capsular bag, the diameter of the sulcus or the diameter of the anterior chamber angle.

Additionally or alternatively, the actuator may be configured to simultaneously rotate the fiber about the longitudinal axis of the optical fiber and to axially move the optical fiber along the longitudinal axis. Thereby, the beam emitter may perform a thread-like movement. In other words, the beam emitter may perform a helical movement about the longitudinal axis. The OCT apparatus may be configured to conduct a helical OCT scan during the helical movement of the beam emitter.

According to an embodiment, the beam emitter comprises a GRIN lens. According to a further embodiment, the beam emitter comprises a reflector. According to a further embodiment, the optical fiber is retractable from within the tube.

According to an embodiment, the beam emitter is configured to shape the OCT measuring beam such that it has a beam waist at a distance of between 4 mm and 9 mm or between 4 mm and 6 mm from the location of the emitter.

According to exemplary embodiments, the hand tool comprises a phacoemulsificator or provides the function of a phacoemulsificator. To this end, the hand tool may comprise an ultrasonic transducer to vibrate a tip end of the tube or of a needle extending adjacent to the tube.

According to a further embodiment, the phacoemulsificator comprises a hollow needle extending adjacent to the tube.

According to a further embodiment, the phacoemulsificator comprises an ultrasonic transducer, configured to vibrate a tip end of the hollow needle. According to a further embodiment, the hand tool comprises a sheath, wherein the tube and the hollow needle are received within the sheath. According to a further embodiment, the phacoemulsificator comprises an ultrasonic transducer configured to vibrate the tip end of the tube or the tip end of the hollow needle. According to a further embodiment, the tip end includes a needle. According to a further embodiment, the phacoemulsificator comprises a fluid supply. According to a further embodiment, the phacoemulsificator comprises an aspiration line.

Embodiments provide a method which comprises: inserting an OCT probe into an interior of an eye; emitting an OCT measuring beam from the OCT probe located within the eye into plural directions; and receiving OCT measuring light scattered from various tissue structures of the eye with the OCT probe.

The OCT probe is connected to an optical coherence tomography (OCT) apparatus for imaging body tissues. Since the OCT probe is located within the eye, high accuracy measurements of eye tissues are obtainable. In particular, eye tissues located behind the iris can be imaged, and diameters of the sulcus and of the capsular bag can be precisely determined. Based on such measurements, it is possible to select an intraocular lens from a stock of intraocular lenses having different sizes, and the selected intraocular lens can be inserted into the eye through a same opening in the cornea of the eye through which the OCT probe was inserted.

According to a further embodiment, the method further comprises: determining a radius of curvature of the longitudinal axis of the axial end section; and correcting OCT data obtained by the OCT scans depending on the determined radius of curvature.

According to an embodiment, the method further comprises selecting the intraocular lens from a stock of intraocular lenses having different diameters based on the determined diameter. According to a further embodiment, the inserting of the intraocular lens into the eye comprises inserting the intraocular lens into one of the anterior chamber of the eye, the posterior chamber of the eye and the capsular bag of the eye. According to a further embodiment, the method further comprises retracting the OCT probe before the inserting of the intraocular lens. According to a further embodiment, the method further comprises generating an opening in a cornea of the eye and inserting the OCT probe through the opening in the cornea into the interior of the eye. According to a further embodiment, the method further comprises inserting the intraocular lens into the eye through the opening.

According to embodiments, a hole is formed in the crystal lens of the eye, and the OCT probe is inserted into this hole to measure the diameter of the capsular bag from within the crystal lens. Again, an intraocular lens may be selected from a stock of intraocular lenses having different sizes, and the selected intraocular lens may be inserted into the capsular bag after removal of the crystal lens.

According to a further embodiment, the method further comprises removing of the lens. According to a further embodiment, the removing of the lens comprises phacoemulsification. According to a further embodiment, the method comprises inserting an intraocular lens into a capsular bag of the eye. According to a further embodiment, the moving of the optical fiber comprises bending a distal end of the optical fiber. According to a further embodiment, the bending of the distal end of the optical fiber comprises oscillating a distal end portion of the optical fiber. According to a further embodiment, the OCT measuring beam is emitted in a direction transverse to a direction of extension of the axial end section.

According to a further embodiment, a GRIN lens is attached to a distal end of the optical fiber. According to a further embodiment, the GRIN lens carries a reflecting surface directing the OCT measuring beam into a direction transverse to the direction of extension of the distal end portion of the optical fiber. According to a further embodiment, the distal end portion of the tube comprises a curved axial section.

According to a further embodiment, the curved axial section has a same curvature over a length of between 2 and 8 mm, or between and 5 mm, or between 2 and 3 mm. According to a further embodiment, the curved axial section has a radius of curvature of between 1 and 6 mm, or between 2 and 5 mm, or between 1 and 3 mm, or between 1 and 2 mm.

According to a further embodiment, the tube is integrated with a phacoemulsificator. According to a further embodiment, the method further comprises retracting the optical fiber from within the tube before performing phacoemulsification with the phacoemulsificator.

According embodiments, the surgical instrument system is configured to carry out the embodiments of the method described herein.

According to further embodiments, the surgical instrument system is configured to perform the method according to the embodiments of the method described herein.

BRIEF DESCRIPTION OF THE DRAWINGS

The forgoing as well as other advantageous features will be more apparent from the following detailed description of exemplary embodiments of the invention with reference to the accompanying drawings. It is noted that not all possible embodiments necessarily exhibit each and every, or any, of the advantages identified herein.

FIG. 2A is a schematic illustration of the distal end portion of the tube of the surgical instrument shown in FIG. 1;

FIG. 2C is a schematic illustration of the insertion process of the distal end portion of the tube of the surgical instrument shown in FIG. 1;

FIG. 2D is a schematic illustration of the insertion process of the distal end portion of the tube of the surgical instrument shown in FIG. 1;

FIG. 3 is an illustration of a method of performing an OCT measurement of an anterior chamber of an eye;

DETAILED DESCRIPTION OF EXEMPLARY EMBODIMENTS

Figure 1:
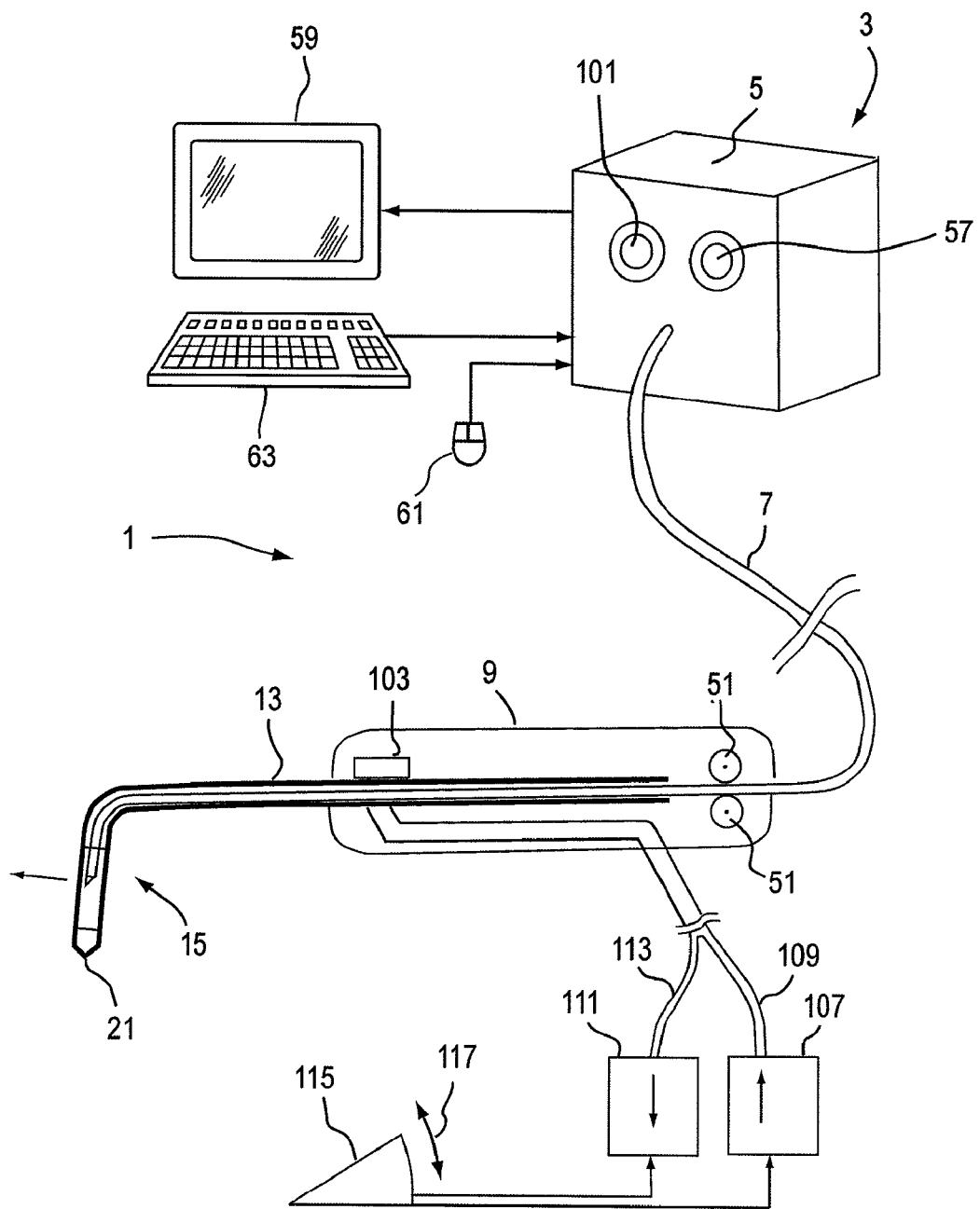
FIG. 1 is a schematic illustration of a surgical instrument system according to an embodiment of the invention.

In the exemplary embodiments described below, components that are alike in function and structure are designated as far as possible by alike reference numerals. Therefore, to understand the features of the individual components of a specific embodiment, the descriptions of other embodiments and of the summary should be referred to.

FIG. 1 is a schematic illustration of a surgical instrument system 1 according to an exemplary embodiment. The surgical instrument system 1 comprises an optical coherence tomography (OCT) apparatus 3 including an optical interferometer received in a housing 5 (not shown in detail in FIG. 1). The interferometer includes a reference arm and a probe arm. The probe arm is provided and extended by an optical fiber 7. The optical fiber 7 comprises a fiber core (not illustrated in FIG. 1) for transmitting OCT measuring light of the OCT apparatus 3. The fiber 7 extends through a hand piece 9 of a hand tool. The hand tool is manipulated by a surgeon. The hand tool comprises a tube 13 extending away from the hand piece 9, wherein the optical fiber 7 is received within the tube 13 and extends through the tube 13 towards a distal end portion 15 of the tube 13.

FIG. 2A is a more detailed cross-sectional view of the distal end portion 15 of the tube 13. The distal end portion 15 comprises a longitudinal axis 14. The longitudinal axis 14 is curved. The distal end portion 15 further comprises a curved axial section 12 extending over a length L. The length L may for example be within a range of 2 mm to 8 mm, within a range of 2 mm to 6 mm, or within a range of 2 mm and 5 mm, or within a range of 2 mm and 3 mm.

For each point on the longitudinal axis 14 within the curved axial section 12, the radius of curvature of the longitudinal axis 14 is within a range of 1 mm to 6 mm, or within a range of 2 mm to 5 mm, or within a range of 1 mm to 3 mm or within a range of 1 to 2 mm. The radius of curvature may be constant within the curved axial section 12. Alternatively, the radius of curvature may vary within the curved axial section 12.

The distal end portion 15 further comprises an axial end section 10, which is located distal to the curved axial section 12. The axial end section 10 may be in contact with the curved axial section 12.

A length of the axial end section 10 may be between 2 mm and 7 mm, or between 5 mm and 7 mm, or between 3 mm and 6 mm, or between 3 mm and 4 mm.

The distal end portion 15 further comprises a proximal axial section 34, which is located proximal to the curved axial section 12. The proximal axial section 34 may be in contact with the curved axial section 12. A proximal end of the proximal axial section is the proximal end 30 of the distal end portion 15. The proximal end 30 may be defined as a location, which is located at the opening the when the distal end portion has been inserted into the eye.

For each point on the longitudinal axis 14 within the proximal axial section 34, the radius of curvature of the longitudinal axis may be greater than 15 mm, in particular greater than 20 mm or greater than 30 mm.

A length of the proximal axial section 34 may be between 3 mm and 6 mm, or between 4 mm and 5.5 mm.

The interior side walls 26 of the axial end section 10 are oriented parallel to the longitudinal axis 14 within the axial end section 10. Furthermore, an outer diameter of the optical fiber 7 and an internal diameter of the interior side wall are adapted such that the interior side walls serve as a guide for the optical fiber. Thereby, a reflecting prism 37, which is attached to the optical fiber 7 via a GRIN lens 31 is located at well defined positions during the scanning process.

Therefore, in case multiple B-scans are acquired at multiple axial positions, the scan planes are oriented substantially parallel to each other. In other words, the scan planes only slightly deviate from an optimal parallel orientation relative to each other. Thereby, precise measurements of interior structures of the eye are obtainable.

The distal end portion 15 may be made of metal and/or of plastic material. Thereby, the tube may provide a suitable rigidity to maintain its shape under usage. For example, the bending stiffness of the distal end portion 15 of the tube 13 may be such that the distal end portion 15 is insertable into the eye through an opening in the cornea of the eye. The tip end 21 of the tube 13 may be pointed such that the tip end may be used to form the opening in the cornea. For example, the tip end may comprise a knife portion or sharp edge 105.

The axial end section 10 comprises a transparent tubular section 23. The transparent tubular section 23 may be made of glass and/or transparent plastic material. The transparent tubular section 23 is transparent around its full perimeter and along a full length L1 of the transparent tubular section 23.

Accordingly, OCT measuring light of the OCT measuring beam is transmittable through the transparent tubular section 23 from inside the tube 13 to outside the tube 13. Furthermore, it is possible to conduct OCT-scans from each point along the longitudinal axis within the transparent tubular section 23.

A fiber core 25 and a fiber cladding 27 of the fiber 7 extend through the distal end portion 15 of the tube 13 towards the tip of the distal end portion 15. A tip end 29 of the fiber is coupled to a gradient index (GRIN) lens 31, which expands OCT measuring light supplied through the fiber 7 from the OCT apparatus 3 to shape a measuring beam 33 emitted from a front end 35 of the GRIN lens 31. A reflecting prism 37 is mounted to the front end 35 of the GRIN lens 31 and reflects the measuring beam such that is emitted in a direction 41 transverse to a direction of extension 42 of the distal end portion of the tube. An angle formed between the directions 41 and 42 can be 90 degrees or greater, such as 100 degrees or 120 degrees, or smaller, such as 80 degrees or 70 degrees.

The GRIN lens 31 is configured such that a beam waist 45 of the OCT measuring beam 33 is formed at a distance d of about 6 mm away from the longitudinal axis 14 of the tube 13 at a position of the reflecting prism 37. Other exemplary values of the distance d are about 4 mm, about 7 mm and about 9 mm. It is also possible that the beam 33 emitted from the GRIN lens 31 is a collimated parallel beam.

As shown in FIG. 1, the OCT apparatus 3 comprises an actuator, such as a pair of rollers 51 driven by a motor, to rotate the fiber 7 about the longitudinal axis of the distal end portion 15. In FIG. 2, this is represented by arrow 47. As a consequence, the GRIN lens 31 and the prism 37 rotate about an axis oriented in the direction 42 as indicated by arrow 49 in FIG. 2. The actuator for rotating the fiber 7 can be located in the housing 5 or in the hand piece 9. Background information with respect to OCT apparatuses which comprise a rotating fiber can be obtained from U.S. Pat. No. 6,134,003, the full disclosure of which is incorporated herein by reference.

Due to the rotation of the beam emitter which comprises the GRIN lens 31 and prism 37, the OCT measuring beam 33 also rotates about the longitudinal axis of the tube 13 at the position of the reflecting prism 37. While rotating the fiber 7 by 360 degrees, the OCT apparatus 3 records one OCT B-Scan.

The hand tool 11 comprises an actuator, such as pair of rollers 51, which are driven by a motor controlled by the OCT apparatus 3 to displace the fiber 7 within the tube 13 along a longitudinal direction of the fiber. FIG. 2 shows an OCT measuring beam 33A in dashed lines which is emitted from the reflecting prism 37 when the actuator 51 has retracted the fiber 7 by an amount of e.g. 3 mm relative to the position indicated in full lines in FIG. 2.

By rotating the fiber 7 about the longitudinal axis and displacing the fiber 7 along the longitudinal axis, the OCT apparatus 3 can systematically scan a volume around the tip end 21 of the tube 13 and perform OCT imaging of that volume. Both, the rotation and the displacement of the fiber can be carried out at constant velocities. Thereby, measuring data can be associated with coordinates of tissue structures based on measuring times. It is, however, also possible to acquire OCT scans at non-constant rotational velocities and/or non-constant velocities of longitudinal movement when the time dependencies of the velocities are known. The data analysis may then be performed depending on the known non-constant rotational velocities and/or the known non-constant velocities of longitudinal movement.

The scan can be started by the surgeon by pressing, for example, a button 57 (shown in FIG. 1) which is mounted on a front panel of the housing 5. A representation of the recorded OCT image of the OCT scan can be displayed, for example, on a monitor 59. Moreover, the surgeon can identify certain features in the image and perform measurements, such as distance measurements, for example by using a mouse 61 or a keyboard 63, to move a cross-hair cursor or other pointer between portions of the image and features within the image. Thereby, distances between different features in the image may be calculated.

Figure 2B:
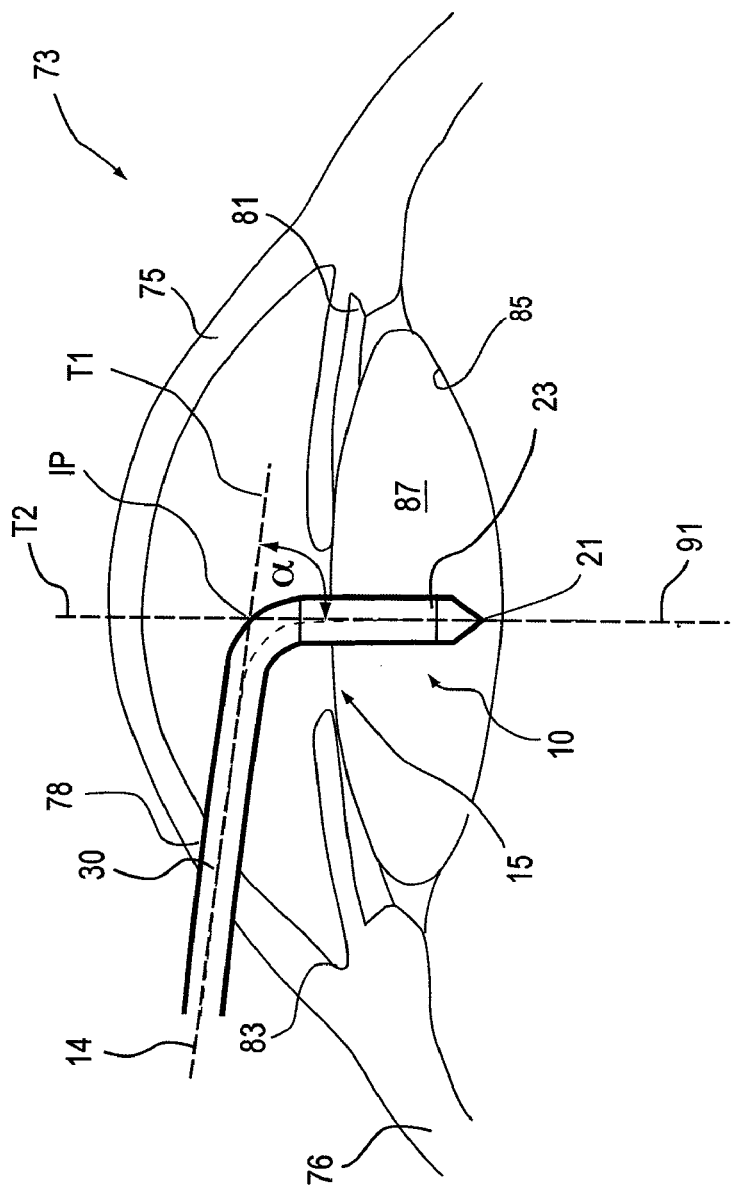
FIG. 2B is a schematic illustration of the distal end portion of the tube of the surgical instrument shown in FIG. 1.

FIG. 2B is a schematic illustration of the distal end portion 15 of the tube 13 in a measurement position within an eye 73. The distal end portion 15 has been inserted into the human eye 73 through an opening 78 in the cornea 75. A first tangent T1 is a tangent to the longitudinal axis at a proximal end 30 of the distal end portion 15. A second tangent T2 is a tangent to the longitudinal axis at a distal end of the distal end portion 15. A bending angle α of the second tangent T2 relative to the first tangent T1 is between 60 and 100 degrees, or between 70 and 100 degrees, or between 70 and 95 degrees, or between 80 and 95 degrees, or between 85 and 90 degrees.

The bending angle α is measured such that it is zero in case the first tangent T1 and the second tangent T2 are parallel to each other, for example, when the distal end portion is straight, and not curved. Depending on the curvature of the longitudinal axis, the first tangent T1 and the second tangent T2 may not form an intersection. In this case, the bending angle α is calculated by projecting both the first tangent T1 and the second tangent on a plane (not illustrated), which is parallel to both the first tangent T1 and the second tangent T2 and the bending angle α is measured from the projected tangents.

A distance of a proximal end 30 of the distal end portion 15 from an intersection point IP of the first tangent T1 and the second tangent T2 is between 4.5 mm and 8 mm or between 5 and 7 mm, or between 5 mm and 6 mm. Furthermore, a distance between the intersection point IP and the tip end 21 is between 5 mm and 8 mm or between 5 and 7 mm, or between 3 mm and 6 mm.

In case the first tangent T1 does not intersect with the second tangent T2, the intersection point IP may be determined for each of the tangents T1, T2 by projecting each of the tangents T1, T2 on the plane, which is oriented parallel to each of the tangents and by determining the points on the first tangent T1 and second tangent T2, respectively, which are closest to the projected intersection point.

Accordingly, as shown in FIG. 2B, it is possible to arrange the distal end portion 15 of the tube 13 within the eye 73 such that the longitudinal axis 14 within the axial end section 10 is aligned with the main axis 91 of the human eye 73.

Furthermore, it is possible to insert the distal end portion 15 through an opening 78, which is located remotely from the main axis 91 of the eye 73. Thereby, the adjustment of the position and orientation of the axial end section 10 is observable by a microscope. An optical axis of the microscope may be oriented substantially parallel to the main axis 91 of the eye 73. Thereby, the adjustment of the position and orientation of the axial end section 10 may be performed with high accuracy. Furthermore, since the opening 78 is located remotely from the main axis 91 of the eye 73, the region of the cornea 75, which is close to the main axis 91 is not affected by the opening 78. Therefore, the opening 78 is less likely to impair vision.

Furthermore, as illustrated in FIG. 2B, the transparent tubular section 23 of the distal end portion 15 allows to image the anterior chamber angle 83 and the ciliary sulcus 81 of the eye 73 with angular scans of 360 degrees. Since the longitudinal axis within the axial end section 10 of the distal end portion is aligned with the main axis 91 of the eye 73, it is possible to obtain OCT data on the structure of the chamber angle 83, the ciliary sulcus 81 and/or the capsular bag 85 around their respective full perimeter. Thereby, it is possible for example to choose an intraocular lens or to manufacture an intraocular lens, which best suits the eye 73.

FIGS. 2C and 2D illustrate the process of inserting the distal end portion 15 through the opening 78 in the cornea 75 of the eye 73. FIGS. 2C and 2D show the eye 73, as it is viewed for example through a microscope, which is used for positioning the axial end section 10 aligned with the main axis 91 of the eye 73. In FIGS. 2C and 2D, the main axis of the eye 91 is oriented perpendicular to the paper plane.

As is illustrated in FIG. 2C, the distal end portion 15 is inserted through the opening 78 in the cornea 45 by moving the axial end section 10 along an insertion direction, which is indicated by arrow 99. After having partially inserted the distal end portion 15, the distal end portion 15 is rotated about a tangent to the longitudinal axis at the proximal end 30 of the distal end portion 15. After or simultaneously with the rotation, the distal end portion 15 is further inserted into the eye 73 until the proximal end 30 is located at the opening 78. Thereby, the axial end section 10 of the distal end portion 15 is guided through the pupil 97 of the eye 73 and the distal end portion 15 is positioned at the measurement position, as indicated in FIG. 2D. The position of the distal end portion 15 within the eye 73 as illustrated in FIG. 2D corresponds to the position as illustrated in FIG. 2B.

An embodiment of an OCT measuring method which can be performed using the surgical instrument system 1 is illustrated with reference to FIG. 3. FIG. 3 shows an anterior portion 71 of a human eye 73 including a cornea 75, limbus 77, iris 79, anterior chamber 89, anterior chamber angle 81, posterior chamber 82, sulcus 83 and capsular bag 85 including a crystal lens 87. The distal end portion 15 of the tube 13 of the hand tool 11 is inserted through an opening in the cornea such that the tip end 21 of the tube 13 and beam emitter 31, 35 are positioned within the anterior chamber 89 of the eye 73. The axial end section 10 of the tube 13 is positioned close to the main axis 91 of the eye 73 and oriented such that the direction 42 is substantially parallel to the main axis 91. With such a position of the hand tool 11, an OCT volume scan is performed as illustrated above. The volume scan includes various tissues of the eye 73 and in particular of the anterior chamber angle 81. A diameter of the anterior chamber angle 83 can be determined by the surgeon by interpreting and analyzing the recorded OCT images displayed on the monitor 59. Based on this determination of the angle diameter, the surgeon may select a suitable phakic intraocular lens from a stock of lenses having different diameters. The selected lens can be inserted into the anterior chamber through the same opening through with the tube 13 was previously inserted.

Figure 4:
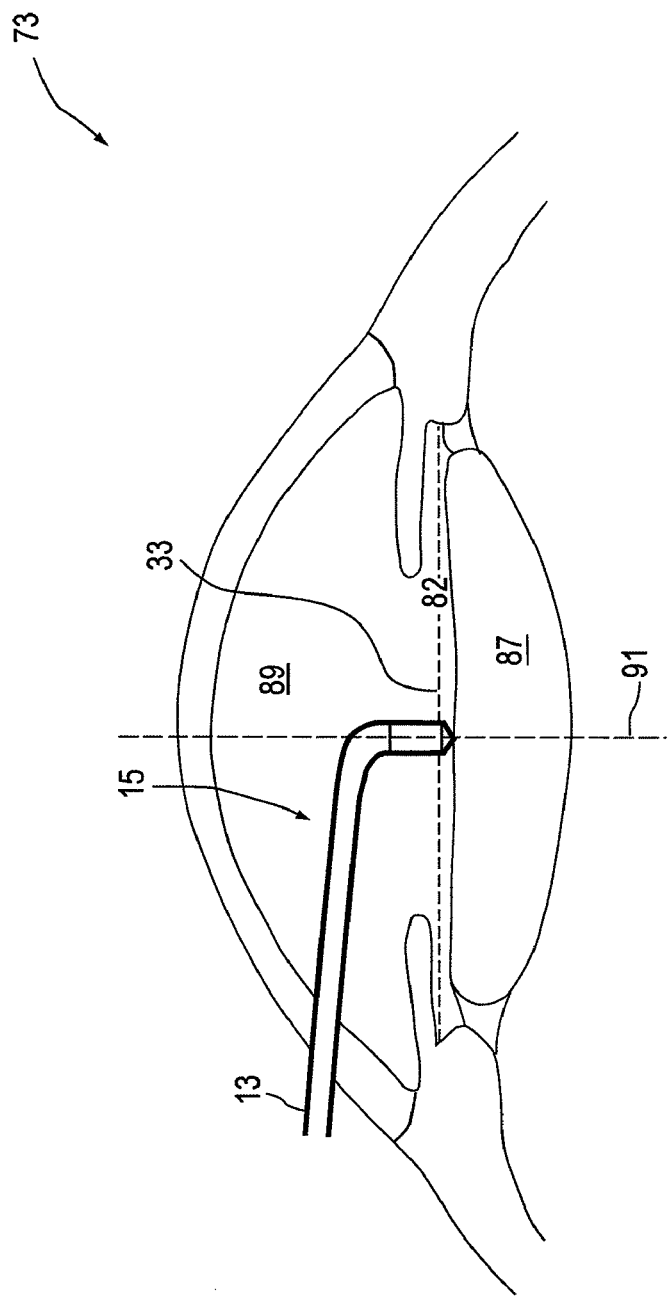
FIG. 4 is an illustration of a method of performing an OCT measurement of a posterior chamber of an eye.

FIG. 4 illustrates a further embodiment of the method. The method illustrated in FIG. 4 is similar to the method illustrated with reference to FIG. 3 above. However, the tip end 21 of the tube 13 is inserted into the posterior chamber 82 of the eye 73 such that it is positioned closer to the crystal lens 87. Thereby, the beam 33, which is emitted from the distal end 21 of the tube 13, reaches the sulcus 81. For this purpose, it might be necessary to push the crystal lens a bit downward as illustrated in FIG. 4. By performing a volume scan at such a position of the tip end 21 of the tube 13, it is possible to image relevant portions of the sulcus 81. This allows to determine the sulcus diameter, also referred to as sulcus-to-sulcus diameter. Again, the surgeon may select a phakic intraocular lens of a suitable size from a stock of lenses having different sizes. The selected lens can be inserted into the posterior chamber through the same opening through which the tube 13 was inserted.

Figure 5:
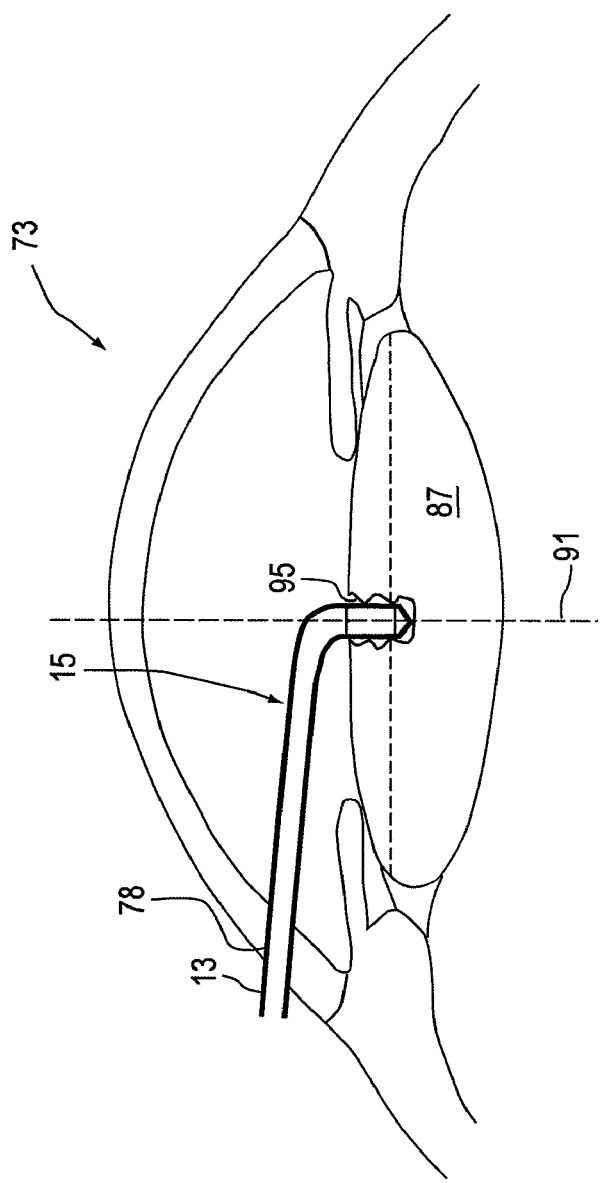
FIG. 5 is an illustration of a method of performing an OCT measurement of a capsular bag of an eye.

FIG. 5 illustrates a further embodiment of an OCT measurement. In this embodiment, the tip end 21 of the tube 13 is positioned within the crystal lens 87 after an aperture or hole 95 has been formed in the lens 87 by a suitable method, such as phacoemulsification. The tube 13 is positioned such that the tip end substantially coincides with the main axis 91 of the lens and is oriented substantially parallel thereto.

An OCT volume scan at such a configuration of the tube 13 records an image of the capsular bag from which the surgeon can determine the diameter of the capsular bag 85 to select a suitable intraocular lens from a stock of lenses having different diameters.

The tube can be retracted from the eye 73, and the crystal lens 87 can be removed, for example by phacoemulsification. Thereafter, the surgeon can insert the selected intraocular lens into the capsular bag 85 through the same opening through which the tube 13 was previously inserted.

The actuator 51 is configured to withdraw the fiber 7 from within the tube 13 to a sufficient extend so that the tip end of the fiber is positioned within the hand piece 9 after the withdrawal. This operation can be controlled by a button 101 mounted on the front panel of the housing 5 or some other input device, for example via the keyboard 63 or the mouse 61.

After the removal of the fiber from within the tube 13, the hand tool 11 can be operated as a phacoemulsificator. For this purpose, the hand tool comprises an ultrasonic transducer 103 coupled to the tube 13 such that the tip end of the tube starts vibrating at a high frequency. The tip end 21 of the tube carries a knife portion or sharp edge 105 suitable to cut emulsified body tissues, such as the crystal lens.

The surgical instrument system further comprises a supply 107 of viscoelastic fluid. The viscoelastic fluid is pumped into the tube 13 via a connecting tube 109. Furthermore, the system 1 comprises a suction apparatus 111 connected to the tube 13 via a connecting tube 113. A foot paddle 115 which can be moved in a direction indicated by an arrow 117 in FIG. 1, or other input device can be used by the surgeon to operate the ultrasonic transducer 103, liquid supply 107 and suction apparatus 111 to perform phacoemulsification. For example, the hole 95 in the crystal lens 87 shown in FIG. 5 can be formed using the hand tool 11. The hand tool can subsequently be used to perform the OCT scan.

While the disclosure has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

The invention claimed is:

1. A surgical instrument system for ophthalmic surgery in an interior of an eye, comprising:
   an OCT apparatus including an interferometer;
   an optical fiber coupled to the OCT apparatus and extending a probe arm of the interferometer, the optical fiber having a tip end;
   a hand tool comprising:
      a hand piece,
      a tube extending away from the hand piece and comprising a distal end portion having a longitudinal axis and a tip end, wherein a distal portion of the optical fiber is received within the tube;
      a beam emitter coupled to the tip end of the optical fiber and configured to emit an OCT measuring beam into an emission direction of the beam emitter; and
      an actuator configured to change the emission direction of the OCT measuring beam relative to the tip end of the distal end portion;
   wherein a first tangent to the longitudinal axis at a proximal end of the distal end portion and a second tangent to the longitudinal axis at the tip end of the distal end portion form a bending angle of the distal end portion of between 60 and 100 degrees; and
   wherein a first distance between an intersection point of the first tangent with the second tangent and the proximal end is between 4.5 mm and 8 mm; and
   wherein a second distance between the intersection point and the tip end of the distal end portion is between 3 mm and 9 mm.

2. The surgical instrument system according to claim 1, wherein the distal end portion comprises an axial end section having a transparent tubular section, which is transparent for measuring light of the OCT measuring beam, and
   wherein a radius of curvature of the longitudinal axis at each point within the transparent tubular section is greater than 15 mm, or greater than 20 mm, or greater than 30 mm.

3. The surgical instrument system according to claim 2, wherein the beam emitter is located within the transparent tubular section and wherein the actuator is configured to displace the beam emitter relative to the tube along the longitudinal axis and over a length of the transparent tubular section.

4. The surgical instrument system according to claim 2, wherein a length of the transparent tubular section is within a range of 1 to 6 mm.

5. The surgical instrument system according to claim 1, wherein the hand piece is configured to rotate the distal end portion about a rotation axis which is aligned with the first tangent.

6. The surgical instrument system according to claim 1, wherein a bending stiffness of the distal end portion is such that the distal end portion is insertable into the interior of the eye through an opening in a cornea of the eye.

7. The surgical instrument system according to claim 1, wherein the tip end of the distal end portion is displaced by less than 1.5 mm or less than 1 mm, when a force of 0.25 N is applied to the tip end of the distal end portion and a proximal end of the distal end portion is held stationary.

8. The surgical instrument system according to claim 1, wherein the actuator is configured to rotate the optical fiber about the longitudinal axis.

9. The surgical instrument system according to claim 1, wherein the actuator is configured to rotate the optical fiber about the longitudinal axis and to move the optical fiber along the longitudinal axis relative to the tube.

10. The surgical instrument system according to claim 1, wherein the beam emitter comprises a GRIN lens.

11. The surgical instrument system according to claim 1, wherein the beam emitter comprises a reflector.

12. The surgical instrument system according to claim 1, wherein the beam emitter is configured to shape the OCT measuring beam such that it has a beam waist at a distance of between 4 mm and 9 mm or between 4 mm and 6 mm from the location of the beam emitter.

13. The surgical instrument system according to claim 1, wherein the optical fiber is retractable from within the tube.

14. The surgical instrument system according to claim 1, wherein the hand tool comprises a phacoemulsificator.

15. The surgical instrument of claim 1, wherein the distal end portion comprises a tubular curved axial section;
  wherein within the distal end portion, the longitudinal axis of the fiber corresponds to the longitudinal axis of the distal end portion.

16. A surgical instrument system for ophthalmic surgery in an interior of an eye, comprising:
  an OCT apparatus including an interferometer;
  an optical fiber coupled to the OCT apparatus and extending a probe arm of the interferometer, the optical fiber having a tip end;
  a hand tool comprising:
    a hand piece,
    a tube extending away from the hand piece and comprising a distal end portion having a longitudinal axis and a tip end, wherein a distal portion of the optical fiber is received within the tube;
    a beam emitter coupled to the tip end of the optical fiber and configured to emit an OCT measuring beam into an emission direction of the beam emitter; and
    an actuator configured to change the emission direction of the OCT measuring beam relative to the tip end of the distal end portion;
  wherein a first tangent to the longitudinal axis at a proximal end of the distal end portion and a second tangent to the longitudinal axis at the tip end of the distal end portion form a bending angle of the distal end portion of between 60 and 100degrees; and
  wherein the tip end of the distal end portion is displaced by less than 1.5 mm or less than 1 mm, when a force of 0.25 N is applied to the tip end of the distal end portion and the proximal end is held stationary.

17. The surgical instrument system according to claim 16, wherein a bending stiffness of the distal end portion is such that the distal end portion is insertable into the interior of the eye through an opening in a cornea of the eye.

18. The surgical instrument system according to claim 16, wherein the distal end portion comprises an axial end section having a transparent tubular section, which is transparent for measuring light of the OCT measuring beam, and
  wherein a radius of curvature of the longitudinal axis at each point within the transparent tubular section is greater than 15 mm, or greater than 20 mm, or greater than 30 mm.

19. The surgical instrument system according to claim 18, wherein the beam emitter is located within the transparent tubular section and wherein the actuator is configured to displace the beam emitter relative to the tube along the longitudinal axis and over a length of the transparent tubular section.

20. The surgical instrument system according to claim 18, wherein a length of the transparent tubular section is within a range of 1 to 6 mm.

21. The surgical instrument system according to claim 16, wherein the hand piece is configured to rotate the distal end portion about a rotation axis which is aligned with the first tangent.

22. The surgical instrument system according to claim 16, wherein the actuator is configured to rotate the optical fiber about the longitudinal axis.

23. The surgical instrument system according to claim 16, wherein the actuator is configured to rotate the optical fiber about the longitudinal axis and to move the optical fiber along the longitudinal axis relative to the tube.

24. The surgical instrument system according to claim 16, wherein the beam emitter is configured to shape the OCT measuring beam such that it has a beam waist at a distance of between 4 mm and 9 mm or between 4 mm and 6 mm from the location of the beam emitter.

25. The surgical instrument of claim 16, wherein the distal end portion comprises a tubular curved axial section;
  wherein within the distal end portion, the longitudinal axis of the fiber corresponds to the longitudinal axis of the distal end portion.

26. A method of conducting an ophthalmic surgery in an interior of an eye by using a surgical instrument system;
  wherein the surgical instrument system comprises:
    an OCT apparatus including an interferometer;
    an optical fiber coupled to the OCT apparatus and extending a probe arm of the interferometer, the optical fiber having a tip end;
    a hand tool comprising:
      a hand piece,
      a tube extending away from the hand piece and comprising a distal end portion having a longitudinal axis and a tip end, wherein a distal portion of the optical fiber is received within the tube;
      a beam emitter coupled to the tip end of the optical fiber and configured to emit an OCT measuring beam into an emission direction of the beam emitter; and
      an actuator configured to change the emission direction of the OCT measuring beam relative to the tip end of the distal end portion;
  wherein a first tangent to the longitudinal axis at a proximal end of the distal end portion and a second tangent to the longitudinal axis at the tip end of the distal end portion form a bending angle of the distal end portion of between 60 and 100 degrees; and
    wherein a first distance between an intersection point of the first tangent with the second tangent and the proximal end is between 4.5 mm and 8 mm; and
    wherein a second distance between the intersection point and the tip end of the distal end portion is between 3 mm and 9 mm;
  wherein the method comprises
    inserting the distal end portion into the interior of the eye; and
    emitting the OCT measuring beam from the beam emitter within the eye.

27. The surgical instrument of claim 26, wherein the distal end portion comprises a tubular curved axial section;

wherein within the distal end portion, the longitudinal axis of the fiber corresponds to the longitudinal axis of the distal end portion.

28. The surgical instrument system according to claim 26, wherein the distal end portion comprises an axial end section having a transparent tubular section, which is transparent for measuring light of the OCT measuring beam, wherein a radius of curvature of the longitudinal axis at each point within the transparent tubular section is greater than 15 mm, or greater than 20 mm, or greater than 30 mm.

29. The surgical instrument system according to claim 28, wherein a length of the transparent tubular section is within a range of 1 to 6 mm.

30. A method of conducting an ophthalmic surgery in an interior of an eye by using a surgical instrument system;

wherein the surgical instrument system comprises:

an OCT apparatus including an interferometer;

an optical fiber coupled to the OCT apparatus and extending a probe arm of the interferometer, the optical fiber having a tip end;

a hand tool comprising:

a hand piece, a tube extending away from the hand piece and comprising a distal end portion having a longitudinal axis and a tip end, wherein a distal portion of the optical fiber is received within the tube;

a beam emitter coupled to the tip end of the optical fiber and configured to emit an OCT measuring beam into an emission direction of the beam emitter; and an actuator configured to change the emission direction of the OCT measuring beam relative to the tip end of the distal end portion;

wherein a first tangent to the longitudinal axis at a proximal end of the distal end portion and a second tangent to the longitudinal axis at the tip end of the distal end portion form a bending angle of the distal end portion of between 60 and 100 degrees; and wherein the tip end of the distal end portion is displaced by less than 1.5 mm, when a force of 0.25 N is applied to the tip end of the distal end portion and the proximal end is held stationary;

wherein the method comprises inserting the distal end portion into the interior of the eye; and emitting the OCT measuring beam from the beam emitter within the eye.

31. The surgical instrument of claim 30, wherein the distal end portion comprises a tubular curved axial section;

wherein within the distal end portion, the longitudinal axis of the fiber corresponds to the longitudinal axis of the distal end portion.

32. The surgical instrument system according to claim 30, wherein the distal end portion comprises an axial end section having a transparent tubular section, which is transparent for measuring light of the OCT measuring beam;

wherein a radius of curvature of the longitudinal axis at each point within the transparent tubular section is greater than 15 mm, or greater than 20 mm, or greater than 30 mm.

33. The surgical instrument system according to claim 32, wherein a length of the transparent tubular section is within a range of 1 to 6 mm.

* * * * *